United States Patent [19]
Cosmescu

[11] Patent Number: 5,797,901
[45] Date of Patent: Aug. 25, 1998

[54] AUTOMATIC ACTIVATION SYSTEM FOR A MEDICAL DIAGNOSTIC MONITORING AND SURGICAL APPARATUS AND METHOD THEREFORE

[76] Inventor: Ioan Cosmescu, 1449 N. 22nd St., Phoenix, Ariz. 85022

[21] Appl. No.: 717,109

[22] Filed: Sep. 20, 1996

[51] Int. Cl.⁶ ........................................ A61B 5/00
[52] U.S. Cl. ........................ 606/10; 606/13; 604/35
[58] Field of Search .................... 606/10, 11, 12, 606/13, 14, 15, 16, 17; 604/35

[56] References Cited

U.S. PATENT DOCUMENTS

| | | | |
|---|---|---|---|
| 4,316,467 | 2/1982 | Muckerheide | 606/12 X |
| 4,580,557 | 4/1986 | Hertzmann | 606/13 X |
| 4,950,267 | 8/1990 | Ishihara et al. | 606/12 |
| 5,071,417 | 12/1991 | Sinofsky | 606/12 X |
| 5,104,391 | 4/1992 | Ingle et al. | 606/11 |
| 5,318,516 | 6/1994 | Cosmescu | 606/10 X |
| 5,334,016 | 8/1994 | Goldsmith et al. | 606/10 X |
| 5,334,191 | 8/1994 | Poppas et al. | 606/12 |
| 5,336,218 | 8/1994 | Linhares | 606/10 |
| 5,350,376 | 9/1994 | Brown | 606/12 |

*Primary Examiner*—Robert L. Nasser
*Attorney, Agent, or Firm*—Snell & Wilmer, L.L.P.

[57] ABSTRACT

An automatic activation system including a method for activating a second apparatus upon detecting the activation of a first apparatus, or an emergency situation or state relating to a first apparatus, is disclosed. The preferred embodiment of the system includes an optical detector or sensor for a fiber optic which, when energized upon detection of a given condition in relation to a first medical apparatus, will trigger a second medical apparatus such as a smoke evacuator or a suction/irrigation unit for a surgical procedure.

16 Claims, 2 Drawing Sheets

AUTOMATIC ACTIVATION SYSTEM FOR A MEDICAL DIAGNOSTIC MONITORING AND SURGICAL APPARATUS AND METHOD THEREFORE

RELATED APPLICATIONS

This patent application is related to, and herein incorporates by reference, my issued U.S. Pat. No. 5,108,389 entitled "Automatic Smoke Evacuator Activator System For A Surgical Laser Apparatus And Method Therefor" and my issued U.S. Pat. No. 5,318,516 entitled "Radio Frequency Sensor For Automatic Smoke Evacuator System For A Surgical Laser And/Or Electrical Apparatus And Method Therefor".

BACKGROUND OF THE INVENTION

1. Field of the Invention

The present invention generally relates to an automatic activation system having a sensor which activates a medical apparatus as a result of sensing or detecting an alarm or emergency associated with another apparatus. More specifically, the present invention relates to an automatic activation system having a fiber optic sensor that will sense when a fiber optic is energized and then in turn activate another medical apparatus including, but not limited to an apparatus such as a smoke evacuation apparatus or suction/irrigation apparatus.

2. Description of the Prior Art

In the past, other sensors have been used to activate medical apparatus. For example, as previously mentioned above, my U.S. Pat. No. 5,108,389 is directed to an automatic smoke evacuator system that is triggered to the "ON" position when the laser cutting beam of a laser surgical apparatus is turned on. The automatic smoke evacuator activator system includes a transmitter means for transmitting a beam of electromagnetic radiation, receiver means for receiving the beam of electromagnetic radiation, switch means located between the transmitter and receiver means for causing the electromagnetic radiation beam to generate an electronic signal, and smoke evacuator means coupled to the receiving means for receiving the electronic signal and activating the smoke evacuator system.

Also, in my U.S. Pat. No. 5,318,516 entitled "Radio Frequency Sensor For Automatic Smoke Evacuator System For A Surgical Laser And/Or Electrical Apparatus And Method Therefor" there is shown a method whereby the radio frequency (RF) energy associated with the generation of RF from an electrosurgery unit (ESU), or a laser surgical apparatus, is detected by an RF sensor. The RF sensor in turn generates a control signal which triggers an automatic control system which ensures that a smoke evacuator system is activated during the same time period that either the laser surgery or ESU is being activated for medical procedures.

The previously described patents are directed to sensors which relate to a very broad range of wavelengths and which are designed to activate a specific medical apparatus, namely a smoke evacuation system to be used in conjunction with an electrosurgery unit (ESU) or surgical laser, in order to remove fumes, smoke, and other debris from the surgical area. The present invention is directed to another type of sensor, namely a fiber optic sensor, which will expand the devices which are capable of being activated by its triggering mechanism, as well as the triggering mechanisms described in the previously described patents, to a large number of applications and apparatus including, but not limited to, a suction/irrigation apparatus. The present invention also functions to broaden the range of units which are measured and monitored to activate any medical apparatus. The second apparatus may be activated not only upon the activation of an ESU or laser surgery unit, but also by a fault condition like an alarm or emergency signal related with the first apparatus.

Although a preferred embodiment of the system and method is described herein with reference to activating a smoke evacuator or suction/irrigation device, the automatic activator system of the present invention is directed to monitoring one device such that it is capable of automatically activating a second device. The monitored device includes any device, that once activated through different means, will trigger the activation of another device thereby automatically activating the second device. The automatic activation system of the present invention also includes a system wherein different conditions detected by one apparatus will trigger a second apparatus due to different sensors for a particular condition, where the first apparatus has no direct electrical connection to the second apparatus.

SUMMARY OF THE INVENTION

It is a principal object of the present invention to provide an automatic activation system which includes a method for activating an apparatus by the detection of a function of another apparatus with no electrical contact between the two apparatus.

It is a further object of the present invention to provide an automatic activation system which includes a method for activating a medical apparatus upon detecting an emergency situation relating to another medical apparatus.

It is still a further object of the present invention to provide an automatic activation system which includes an optical detector or sensor for a fiber optic which, when energized upon detection of a given condition in relation to a first medical apparatus, will trigger another medical apparatus such as a smoke evacuator or suction/irrigation unit for a surgical procedure.

In brief, the automatic activation system of the present invention includes a first medical apparatus with means for generating an output signal during its activation, sensor means for detecting the output signal and in turn emitting a second output signal to a second medical apparatus, and a second medical apparatus that is activated upon receiving the second output signal. The preferred embodiment of this invention is directed toward an automatic activation system which comprises an optical sensor means which includes a fiber optic contained within a housing wherein optic sensors detect laser beams transmitted through the optic fiber. The automatic activation system of the present invention also includes a time delay means for defining an interval of time and delay control means for deactivating the second medical apparatus after the time interval period, upon deactivation of the first medical apparatus. Further, the first medical apparatus may comprise a surgical laser or ESU apparatus and the second medical apparatus may comprise a smoke evacuation means and/or a suction/irrigation apparatus.

The present invention is also directed toward a method for activating a second apparatus by detection of a function of a first apparatus comprising the steps of (1) activating a first apparatus, (2) sensing the activation of the first apparatus by means of a sensor coupled to the first apparatus, (3) sending a signal from the sensor to the second apparatus, and (4) activating the second apparatus upon receiving the signal from the sensor. Here we define "sensor" as being any type of detector which detects and/or monitors a state or condition of one apparatus and then acts to change a state or condition of another apparatus as a result of the state or condition of the first apparatus.

DETAILED DESCRIPTION OF THE PREFERRED EMBODIMENT

Figure 1:
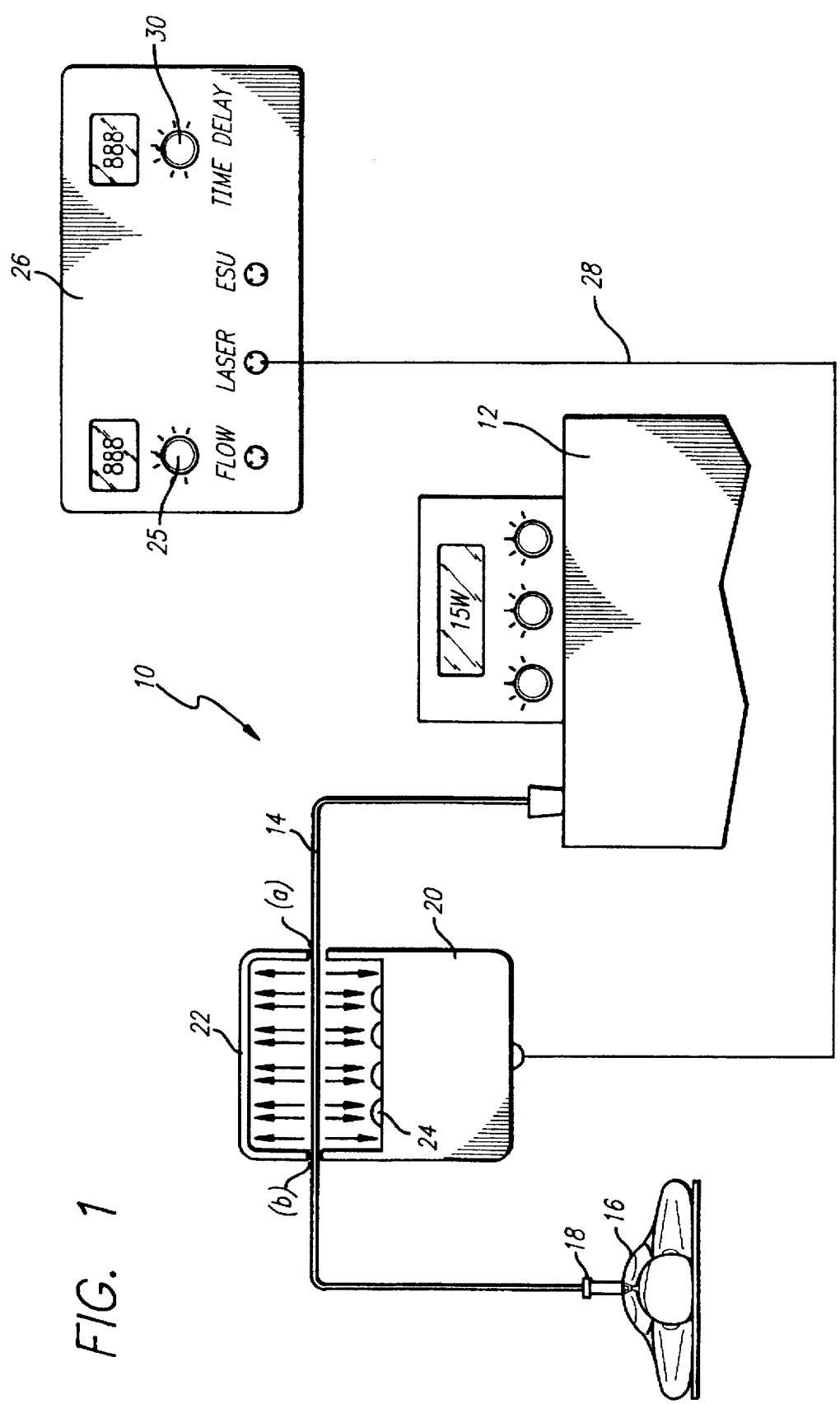
FIG. 1 is a plan view of an automatic activation system in accordance with the present invention showing a surgical laser apparatus incorporating a fiber optic for beam delivery wherein an optical sensor for the fiber optic is coupled to a controller capable of activating a second apparatus.

A plan view of the automatic activation system 10 of the present invention having a fiber optic sensor is shown in FIG. 1. FIG. 1 depicts a surgical laser apparatus 12 which produces a laser beam output signal that is transmitted via a fiber optic 14 to the patient 16.

The laser beam enters the fiber optic 14 upon the activation of a switch on the handpiece 18 or a foot switch (not shown). The fiber optic 14 passes through an optical sensor unit 20, entering the optical sensor unit 20 at point (a) and exiting the optical sensor unit 20 at point (b). The fiber optic 14 is completely covered and isolated from external light between points (a) and (b) of the fiber optic 14 by a housing 22 for the optical sensor unit 20.

Upon activation of the surgical laser apparatus 12, an intense, narrow beam of light is emitted through the fiber optic 14. The optical sensor unit 20 is coupled to a controller 26. The optical sensors 24 contained within the optical sensor unit 20 are designed to be sensitive enough to detect particular laser wave lengths and to sense the leakage of energy associated with the laser wave lengths (which is very small), amplify the original energy, and transform it into an ON-OFF signal.

The ON signal is transmitted to the controller 26 via a conductor 28. The controller 26 can constitute a separate unit, or it can be incorporated into the second apparatus, such as a smoke evacuator or suction/irrigation unit, which is automatically activated as a result of the conductor 28. The ON signal will remain ON for as long as the surgical laser apparatus 12 is activated plus an additional time period associated with a time delay which is connected to the OFF switch. In other words, when the OFF signal is received, the second apparatus connected to the controller 26 will remain "on" for a short predetermined time period before deactivation. The timed delay period for deactivation may be adjusted by a time delay adjustment knob 30 on the controller 26. The flow rate may be adjusted with flow adjustment knob 25.

Figure 2:
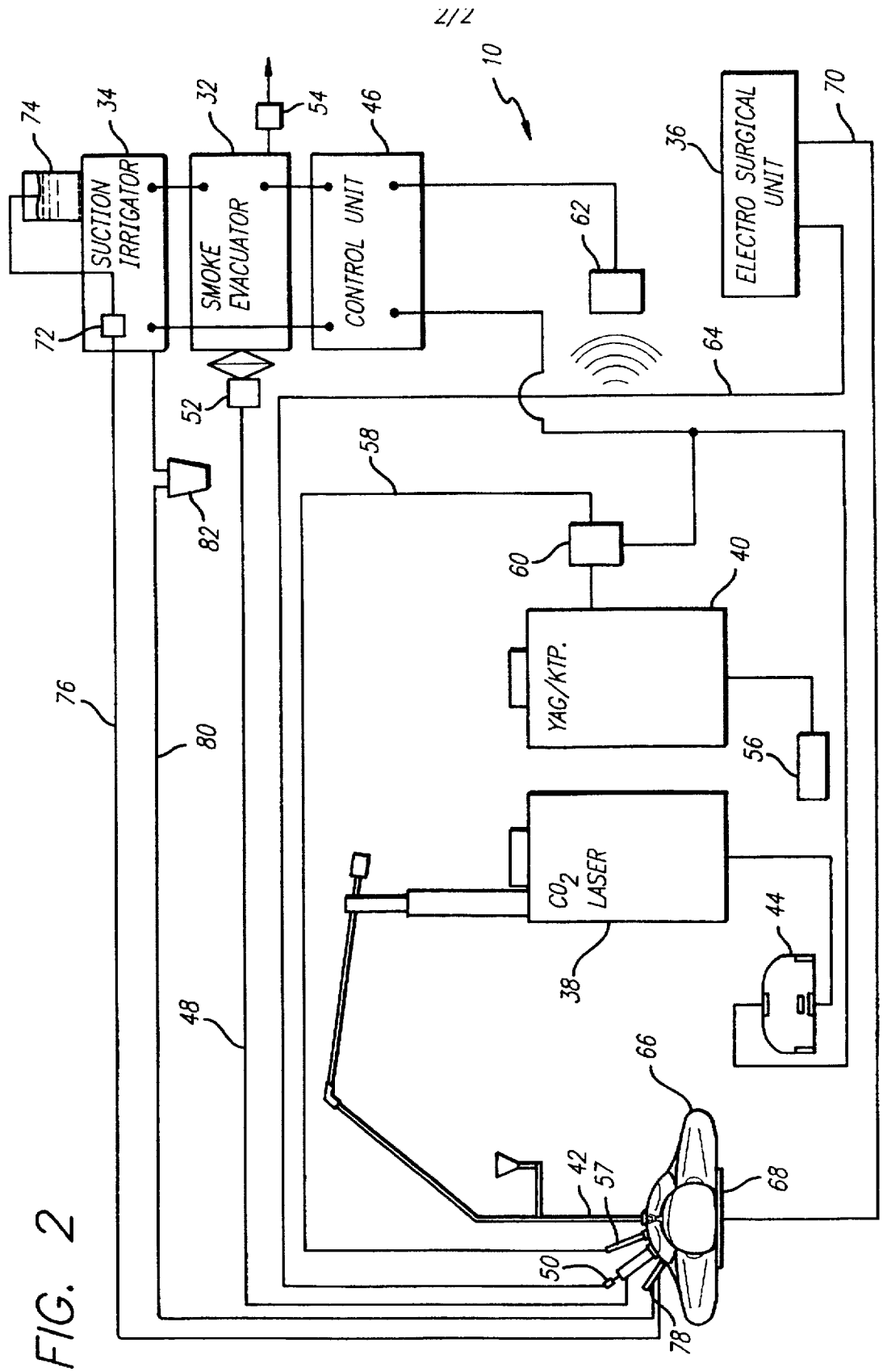
FIG. 2 is a block diagram of the automatic activation system of the present invention for activating a smoke evacuator or suction/irrigation apparatus in relation to a surgical laser or electrosurgery apparatus.

FIG. 2 is a block diagram of the automatic activation system 10 of the present invention for activating a smoke evacuator 32 or suction/irrigation unit 34 in response to detection of a given condition or state associated with an electrosurgery unit 36, a $CO_2$ laser, or other lasers such as YAG, KTP, etc. Three different medical apparatus are designated as the initial medical apparatus which is monitored to detect an emergency situation or defined condition which then triggers activation of a second medical apparatus via a sensor. These three medical apparatus and their automatic activation methods will be addressed below in turn.

A $CO_2$ laser 38 is designated as the first medical apparatus which will activate a second medical apparatus via a sensor. The $CO_2$ laser 38 delivers a laser beam to the patient via a laparoscope 42 or a handpiece (not shown) when the foot switch 44 is activated. The sensor, which is installed on the foot switch 44, delivers the signal that the $CO_2$ laser has been activated to the control unit 46 which in turn will activate the smoke evacuator 32, the suction/irrigation unit 34, or some other medical apparatus.

As previously stated with reference to FIG. 1, the control unit 46 may be a separate, self-contained unit or it may be incorporated into the second medical apparatus that is to be activated. When the smoke evacuator 32 is activated, suction is applied to the proximal end of tubing 48. A cannula is connected to the distal end of tubing 48 for laparoscopic procedures or an electrosurgery (ESU) handpiece 50 is connected to the distal end of tubing 48 for open electrosurgery procedures. A filter and fluid trap 52 are located near the proximal end of tubing 48 for filtering the smoke and debris, and trapping the fluids, from the filter. The clean gas is then passed through the smoke evacuator unit 32 and then through a second filter 54 before being eliminated. The smoke evacuator unit 32 will be activated for as long as the foot switch 44 is activated plus an additional time period that represents a predetermined delay time for deactivating the smoke evacuator unit 32 upon deactivation of the $CO_2$ laser 38. This time OFF delay allows for the smoke to be cleared from the tubing 48.

Other lasers such as YAG and KTP 40 are also designated as the first medical apparatus which will activate a second medical apparatus via a sensor. A second foot switch 56 or handpiece 57 activates the YAG or KTP laser 40 and a laser beam is emitted through fiber optic 58. The optical sensor 60 is coupled to the controller 46 and upon detection of a given condition or state associated with the YAG or KTP laser 40, the optical sensor 60 transmits an ON signal to the controller 46 which in turn activates the smoke evacuator 32 or the suction/irrigation unit 34. Upon deactivation of the YAG or KTP laser 40, there is a delay in deactivation of the smoke evacuator 32 or the suction/irrigation unit 36 as previously described with reference to FIG. 1.

Finally, with reference to FIG. 2, an electrosurgery unit 36 is also designated as the first medical apparatus which will activate a second medical apparatus via a sensor. Upon activation of the electrosurgery unit 36 by a foot switch or hand switch, an output signal is sent to the ESU handpiece 50 via output path 64. Radio frequency (RF) from output path 64 is detected by RF sensor 62. RF sensor 62 then sends an ON signal to the control unit 46 which in turn will activate a second medical apparatus such as the smoke evacuator 32 and/or the suction/irrigation unit 34. During this procedure, the patient 66 is in contact with a patient ground plate 68 which couples to patient ground return path 70 which couples to the electrosurgery unit 36.

When the second medical apparatus to be activated is the suction/irrigation unit 34, the sensors 44, 60, 62 associated with the $CO_2$ laser 38, YAG or KTP laser 40, and electrosurgery unit 36, respectively, will send a signal to the control unit 46 upon activation of the first medical apparatus ($CO_2$ laser 38, YAG or KTP laser 40, or electrosurgery unit 36) but the control unit 46 will only be energized and not activated. When the first medical apparatus, namely the $CO_2$ laser 38, the YAG or KTP laser 40, or electrosurgery unit 36 is deactivated, then the suction/irrigation unit 34 will turn ON for a predetermined period of time. In some situations, such as with electrosurgery, or YAG or KTP laser surgery, the suction/irrigation unit 34 could work simultaneously with the medical apparatus.

Upon activation of the suction/irrigation unit 34, a pump 72 is activated and irrigation fluid is drawn from irrigation fluid container 74, through irrigation tubing 76, to the suction/irrigation handpiece 78. In contrast, when suction is applied with the suction/irrigation handpiece 78, fluid is drawn from the patient 66, through the suction/irrigation handpiece 78 and suction tubing 80, to the fluid canister 82 and then discarded. Once again, time delays for activation and deactivation may be built within the automatic activation system at various points throughout the system.

While the invention has been particularly shown and described with reference to a preferred embodiment thereof, it will be understood by those skilled in the art that changes in form and detail may be made therein without departing from the spirit and the scope of the invention. For example, numerous other medical apparatus which are capable of optical detection may be coupled with an optical sensor which is capable of emitting a signal to activate a second medical apparatus.

I claim:

1. An automatic activation system comprising, in combination:
   a surgical laser apparatus having means for generating a laser beam;
   a fiber optic for receiving said laser beam upon activation of the laser surgical apparatus; and
   optical sensor means for detecting said laser beam being transmitted through an exterior surface said fiber optic and in turn emitting an output signal to a medical apparatus having means for activation upon receiving said output signal from the optical sensor means.

2. The automatic activation system of claim 1, further comprising a controller for receiving said output signal and transmitting said output signal to said medical apparatus.

3. The automatic activation system of claim 1, wherein said medical apparatus comprises at least one of a smoke evacuator means and a suction/irrigation apparatus.

4. The automatic activation system of claim 1, further comprising:
   time delay means defining an interval of time; and
   delay control means for deactivating said medical apparatus after said interval of time upon discontinuation of the activation of said surgical laser apparatus.

5. The automatic activation system of claim 1, wherein said optical sensor means comprises a housing which completely encloses a length of said fiber optic, and at least one optical sensor contained within said housing having means for detecting laser wave lengths transmitted through said optic fiber.

6. An automatic activation system comprising, in combination:
   a first apparatus having means for generating an output signal during activation of said first apparatus that can be optically detected:
      a fiber optic for receiving said output upon activation of the first apparatus; and
      optical sensor means for detecting said output signal being transmitted through said fiber optic and in turn emitting an output signal to a second apparatus having means for activation upon receiving said output signal from the optical sensor means, wherein said optical sensor means comprises a housing which completely encloses a length of the fiber optic and at least one optical sensor contained within the housing having means for detecting laser wave lengths transmitted through the optic fiber.

7. The automatic activation system of claim 6 further comprising a controller having means for receiving said output signal and means for transmitting said output signal to said second apparatus.

8. The automatic activation system of claim 6 wherein said first apparatus comprises a surgical laser apparatus.

9. The automatic activation system of claim 6, wherein said second apparatus comprises at least one of a smoke evacuator means and a suction/irrigation apparatus.

10. The automatic activation system of claim 6, further comprising:
    time delay means for defining an interval of time; and
    delay control means for deactivating said second apparatus after said interval of time upon discontinuation of said output signal.

11. A method for activating a second apparatus by detecting activation of a first apparatus having means for generating a laser beam comprising the steps of:
    activating the first apparatus to generate said laser beam;
    channeling said laser beam to travel through a fiber optic;
    sensing the activation of said first apparatus by means of an optical sensor capable of detecting laser wave lengths transmitted through an exterior surface of said fiber optic where the optical sensor comprises a housing completely enclosing a length of the fiber optic and at least one optical sensor contained within the housing having means for detecting laser wave lengths transmitted through the optic fiber;
    sending a signal from said optical sensor to the second apparatus to activate the second apparatus; and
    activating the second apparatus upon receiving the signal from the optical sensor.

12. The method of claim 11, further comprising the step of providing at least one of a foot switch and handpiece switch for activating said first apparatus.

13. The method of claim 11, further comprising the step of providing a time delay means for deactivating said second apparatus at a predetermined time period following deactivation of said first apparatus.

14. A method for activating a second apparatus by detecting activation of a first apparatus having means for generating a laser beam comprising the steps of:
    activating the first apparatus to generate said laser beam;
    channeling said laser beam to travel through a fiber optic;
    sensing the activation of said first apparatus by means of an optical sensor capable of detecting laser wave lengths transmitted through an exterior surface of said fiber optic where the optical sensor comprises a housing completely enclosing a length of the fiber optic and at least one optical sensor contained within the housing having means for detecting laser wave lengths transmitted through the optic fiber;
    sending a signal from said optical sensor to a controller;
    receiving the signal from the optical sensor at the controller; and
    sending a second signal from said controller to said second apparatus to activate said second apparatus.

15. The method of claim 14, further comprising the step of providing at least one of a foot switch and handpiece switch for activating said first apparatus.

16. The method of claim 14, further comprising the step of providing a time delay means for deactivating said second apparatus at a predetermined time period following deactivation of said first apparatus.

* * * * *